United States Patent [19]

Minnich

[11] Patent Number: 5,762,606

[45] Date of Patent: Jun. 9, 1998

[54] COMBINED EYELID RETRACTOR AND EYE FLUSHING DEVICE

[76] Inventor: Thomas E. Minnich, 5209 Timber Creek Cir., North Little Rock, Ark. 72116

[21] Appl. No.: 857,962

[22] Filed: May 16, 1997

[51] Int. Cl.$^6$ .................................... A61B 17/02
[52] U.S. Cl. .................. 600/205; 600/236; 600/201; 604/289
[58] Field of Search ................... 600/236, 201, 600/205, 208, 210, 235, 184; 604/289, 294, 295, 297, 300, 302, 290, 313; 606/162

[56] References Cited

U.S. PATENT DOCUMENTS

| | | | |
|---|---|---|---|
| 4,131,115 | 12/1978 | Peng | 128/249 |
| 4,543,096 | 9/1985 | Keene | 604/300 |
| 4,798,599 | 1/1989 | Thomas | 604/290 |
| 4,981,479 | 1/1991 | Py | 604/302 |
| 5,030,214 | 7/1991 | Spector | 604/301 |
| 5,108,412 | 4/1992 | Krumeich et al. | 606/166 |
| 5,171,254 | 12/1992 | Sher | 600/236 X |
| 5,171,307 | 12/1992 | Sanning | 661/327 |
| 5,201,726 | 4/1993 | Kirkham | 604/294 |
| 5,387,201 | 2/1995 | Fowler | 604/290 |
| 5,433,190 | 7/1995 | Sunlap | 600/236 |
| 5,556,417 | 9/1996 | Sher | 600/236 |
| 5,599,330 | 2/1997 | Rainin | 604/289 X |
| 5,611,788 | 3/1997 | Marchment | 604/300 X |

OTHER PUBLICATIONS

Clinical Procedures In Emergency Medicine, 2nd Ed. W.B.Saunders Co. Philadelphia, PA Robert Hedges, Author pp. 998–1011 (1991).

Primary Examiner—Jeffrey A. Smith
Attorney, Agent, or Firm—Trent C. Keisling; Head, Johnson & Kachigian

[57] ABSTRACT

A combined eyelid retracting and eye flushing device that permits an operator to retract the upper eyelid of a patient for selective eye flushing or other treatment. The device comprises a frame with spaced apart ends. One end forms an integral handle and the other end defines a peripheral edge that forms an arcuate lip for securing the eyelid to the frame. A plurality of spaced apart orifices penetrate the lip to distribute suction along the entire edge surface. An integral flushing system attached to the frame near the lip comprises an irrigator with a hollow stem protruding outwardly from one side of the frame and an aspirator with a hollow stem protruding oppositely. The irrigation stem terminates in a nozzle that selectively sprays liquids upon the eye and the aspiration stem terminates in a receptive orifice that drains run-off liquids and entrained contaminants therefrom. The lip, irrigator and aspirator all connect to a plurality of channels housed inside the frame. The channels establish fluid flow communication through the frame from the lip, irrigator and aspirator to external vacuum suction, liquid and storage sources. When the device is deployed, an operator aligns the lip along the upper eyelashes and the aspirator stem adjacent the inner terminus of the palpebral fissure. The upper eyelid is then seated against the frame edge with vacuum suctioning through the lip. The upper eyelid is retracted as the frame rests upon the patient's forehead and superciliary arch.

18 Claims, 6 Drawing Sheets

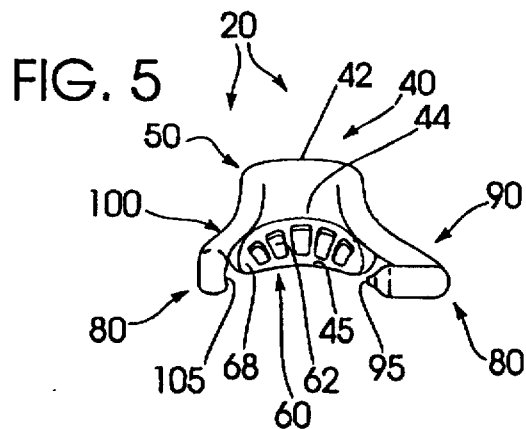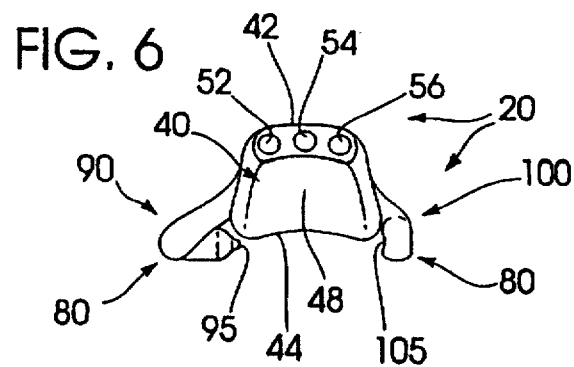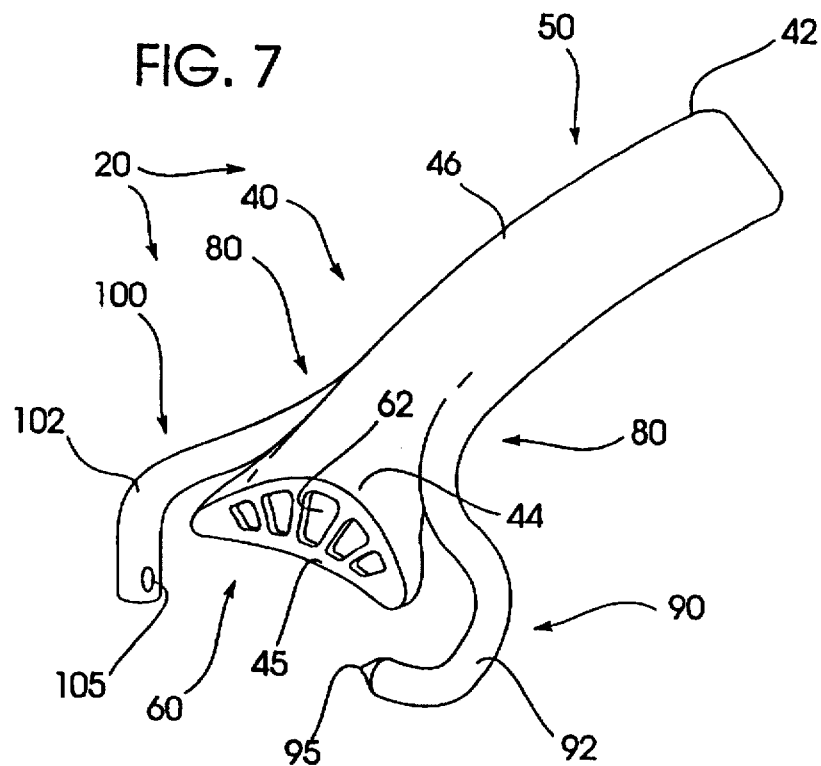

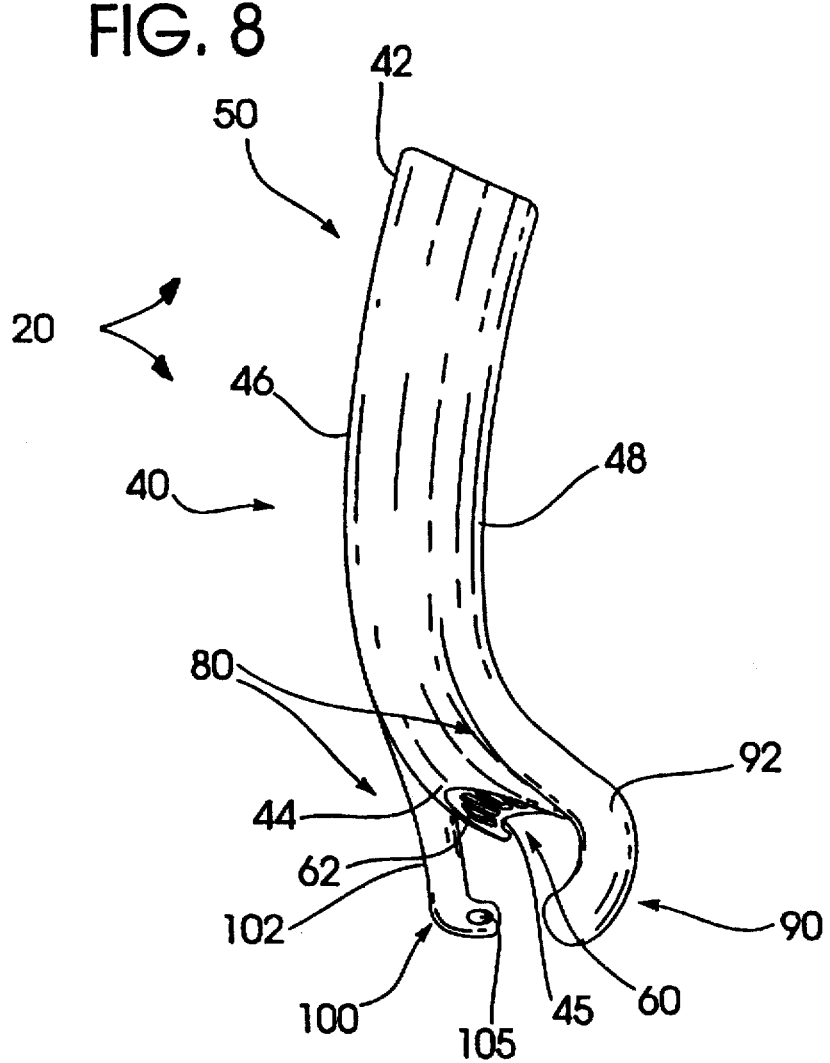

COMBINED EYELID RETRACTOR AND EYE FLUSHING DEVICE

BACKGROUND OF THE INVENTION

I. Field of the Invention

The present invention relates generally to devices for holding human eyelids open. More particularly, the present invention relates to a device that retracts a human eyelid while selectively irrigating and aspirating the eye surface beneath. Relevant prior art may be found in U.S. Class 128, subclass 249, Class 604, subclasses 290 and 301, and Class 606, subclass 327 and others.

II. Description of the Prior Art

As will be recognized by those skilled in the art, manipulation of the eye and eyelid must always be performed carefully to prevent discomfort and serious damage to the eye. This is especially true if the eyelids are to be held open so that the eye may be operated upon or flushed or the like.

Over the years, several different types of tools have evolved to make eyelid retraction and eye flushing easier. These known prior art devices for retracting eyelids can be generally categorized as either surgical specula or emergency quick-flushing devices.

The former devices are generally stainless steel mechanical holders that retract eyelids during surgery while the latter are relatively simple devices that permit a liquid to be sprayed onto the eye to flush contaminants therefrom. Specula are a common tool used by Ophthalmologists during eye surgery to hold the patient's eyelids apart. In use, the typical speculum employs mechanical sleeves that fit around the patient's upper and lower eyelids to push them apart during surgery as shown in U.S. Pat. No. 5,433,190.

As may well be imagined, specula are difficult to use properly and require a great deal of care during their deployment since they present unique problems. For example, at least a portion of a typical speculum sleeve actually fits under the eyelid itself As may well be imagined, this arrangement is not suitable for use with conscious patients. As the speculum is opened, this arrangement can cause the speculum to drag across the patient's eye. In order to avoid unnecessary eye irritation and possible injury, great care must be taken when using conventional specula to retract eyelids. On the other hand, flushing devices are generally easier to use than specula or other surgical devices.

Eye flushing devices generally permit the user to flush the eye to remove contaminants. For example, U.S. Pat. Nos. 5,387,201 issued to Fowler, 5,030,214 issued to Spector, and 4,798,599 issued to Thomas, all show devices with mechanical eyelid holders that keep the eyelids open while a fluid is sprayed upon the eye. The latter two also have gravity fed channels or paths for the evacuation of the fluid and/or debris from the eye.

Other patents of general interest include U.S. Pat. Nos. 5,201,726, 5,171,307 and 4,131,115, also directed to eye flushing devices. The first two show devices that irrigate an eye and provide a separate containment area for storing run-off fluids and/or debris. The latter also has an eyelid turning structure that grips and turns both eyelids so that they may be washed interiorly. However, all of these devices are designed to be used by conscious victims. Furthermore, the devices with eyelid holders appear to be difficult to manipulate properly.

Moreover, some situations are incompatible with preferred speculum operating environments or typical eye flushing scenarios. For example, emergency medical technicians (EMT's) are often pressed for time and they are also often ill-equipped to administer first aid to eye trauma victims at an accident site. Unconscious victims are especially problematic because they cannot assist the technician or respond to medical interrogations. Occasionally, eye injuries may be inadvertently aggravated if first aid givers forcefully open the victim's eyelids to check the victim. This forceful eyelid opening can destructively drag trapped debris and the like across the victim's eye and cause more damage to the eye. Of course, the same reasoning also applies to anesthetized patients as well.

Thus, an user-friendly, easily manipulated eyelid retracting device would be a beneficial improvement. Such a device should permit the upper eyelid to be easily retracted so that the eye could be accessed for flushing or other treatments.

A particularly useful eyelid retracting device would avoid exerting downward pressure upon the eye during placement and eyelid retraction. Such a device would enable an operator to retract at least the victim's upper eyelid without causing any further eye injury. Also, a desirable device would enable an operator to open the victim's eyelid with one hand and without actually contaminating the eye itself by touching the eye during the opening procedure.

An integral alignment mechanism for the retraction device would also be desirable. An alignment mechanism would increase the speed and efficiency of the EMT's while ensuring proper placement of the retracting elements. Thus, the operator would be able to quickly place the retraction device properly.

A cooperative flushing system integrally associated with the retraction mechanism would also be beneficial. Of course, the flushing system would need to be selectively operational. Such a system could be used by EMT's and the like to immediately flush the eyes of trauma victims without causing further eye damage. Moreover, such a system would permit periodic flushing in unconscious victims to prevent corneal drying.

SUMMARY OF THE INVENTION

My combined eyelid retracting and eye flushing device overcomes the perceived problems with prior art devices. The device permits an operator to retract the upper eyelid of a patient for selective eye flushing or other treatment. The device works equally well on conscious and unconscious patients. Moreover, it can be easily employed by EMT's and the like to avoid unnecessary eye injury when treating eye trauma victims.

The retractor can be quickly aligned and secured to the upper eyelid of a patient. The eyelid is secured to the retractor via vacuum suction from an external source. The eyelid may then be retracted to expose the eye when the operator rotatably moves the device. Importantly, the placement and retraction of the eyelid can be accomplished with a single hand and without exerting downward pressure upon the eye. During and after eyelid retraction, the eye may be constantly flushed by an integral flushing system. The flushing system comprises an irrigator that sprays liquids from an external source into the eye and an aspirator that captures the run-off liquids and any entrained contaminants and stores them externally.

The device comprises an elongated, resilient frame with spaced apart ends. The frame forms an integral handle abutting one end of the frame and extending interiorly. The other frame end has a peripheral edge that forms an arcuate lip for securing the eyelid to the frame. Preferably, a plurality of spaced apart orifices penetrate the lip so that the vacuum suction through the lip is distributed along the entire surface of the edge. The flushing system is also integrally attached to the frame near the lip end.

In the preferred embodiment, the irrigator comprises a hollow stem that protrudes outwardly from one side of the frame and the aspirator comprises another hollow stem that protrudes outwardly from the other side of the frame. When the device is placed on a patient, the irrigation stem protrudes from the outer side of the frame and the aspiration stem protrudes from the inner side. The terminal end of the irrigation stem forms a nozzle adjacent the outer side of the lip. The distal end of the aspiration stem forms a receptive orifice adjacent the inner side of the lip.

The lip, irrigator and aspirator all connect to a plurality of channels housed inside the frame. The channels establish fluid flow communication through the frame from the lip, irrigator and aspirator to external vacuum suction, liquid and storage sources. The handle end comprises terminal nipples adapted to couple the internal channels to conventional medical tubing or the like extending to conventional vacuum suction, liquid and storage sources.

Preferably, one channel provides suction for the lip. Another channel provides liquids for the irrigator and another provides communication to the external storage for the aspirator. The aspirator may be powered by gravity, vacuum suction or the like. Of course, if vacuum suctioned, the aspirator could use the same suction source as the lip if desirable. On the other hand, the aspirator could have a separate vacuum suction and storage source. In the preferred embodiment, the lip, irrigator and aspirator are all separately supplied and the aspirator is vacuum suctioned.

When the device is deployed, the lip is placed along the lower edge of the upper eyelid adjacent the eyelashes by an operator. The operator may easily align the lip along the upper eyelashes and the aspirator stem adjacent the inner end of the palpebral fissure or the inner end of the upper-to-lower eyelid Juncture. The upper eyelid is then seated against the frame edge with vacuum suctioning through the lip. The operator may then retract the upper eyelid by moving the frame handle so that it rests upon the patient's forehead and against the superciliary arch.

After the eyelid is seated against the lip, flushing may begin. Preferably, flushing is selectively controlled via conventional controls commonly used with liquid dispensing and vacuum suctioning. The irrigator sprays the liquid across the eye while the aspirator drains run-off and entrained debris from the eye. While the closed eye may be flushed as it is opened, it is generally preferable to wait until the eyelids have been retracted before beginning eye flushing.

Thus, a basic object of the present invention is to provide an eyelid retraction and eye flushing device that does not exert downward pressure upon the eye during eyelid retraction or flushing.

Another basic object of the present invention is to provide an eyelid retraction device that does not further injure a victim's eye when debris is trapped under the eyelid.

A primary object of the present invention is to provide an eyelid retraction device that may be used by EMT's and the like to quickly align and retract a victim's eyelid using conventional vacuum suctioning.

Another primary object of the present invention is to provide a device that may be used by EMT's and the like for quickly treating eye trauma victims.

A related object of the present invention is to provide a device that may be used by EMT's and the like for treating unconscious eye trauma victims while avoiding unnecessary eye injury.

A related object of the present invention is to provide a flushing system that captures run-off liquids and any entrained debris separately.

Another basic object of the present invention is to provide a means for maintaining corneal hydration while the eyelid is retracted.

Another object of the invention is to provide an integral eyelid retractor and flushing system that enables operators to efficiently retract an eyelid while selectively flushing the eye.

Yet another primary object of the present invention is to provide an eyelid retractor and flushing system that may be easily employed upon unconscious victims or anaesthetized patients, permitting optical access through the cornea into the eye interior.

Another related object of the present invention is to provide an integral flushing system that selectively irrigates the eye to wash contaminants therefrom.

Another related object of the present invention is to provide an integral flushing system that selectively aspirates the eye to remove run-off liquids and contaminants therefrom.

A primary object of the present invention is to use vacuum suctioning to secure an eyelid to a retractor for movement. It is a feature of the present invention that the vacuum suctioning is spread over a substantial portion of the eyelid to avoid overly stressing the eyelid and thereby causing injury.

Yet another object of the present invention is to avoid contaminating the eye during opening.

A related object of the present invention is to provide a device that permits an operator to open a victim's eye using only one hand.

These and other objects and advantages of the present invention, along with features of novelty appurtenant thereto, will appear or become apparent in the course of the following descriptive sections.

BRIEF DESCRIPTION OF THE DRAWING

In the following drawings, which form a part of the specification and which are to be construed in conjunction therewith, and in which like reference numerals have been employed throughout wherever possible to indicate like parts in the various views:

FIG. 5 is a bottom plan view of the invention;

FIG. 6 is a top plan view of the invention;

FIG. 7 is an isometric view of the invention;

FIG. 8 is an isometric view of the invention, taken generally from the side;

DETAILED DESCRIPTION

Figure 1:
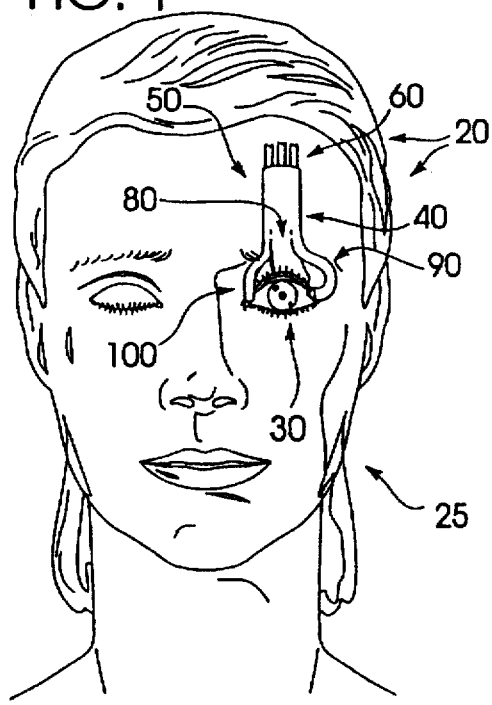
FIG. 1 is an environmental view taken generally from the front and showing the combined eyelid retractor and eye flushing device in use.
Figure 2:
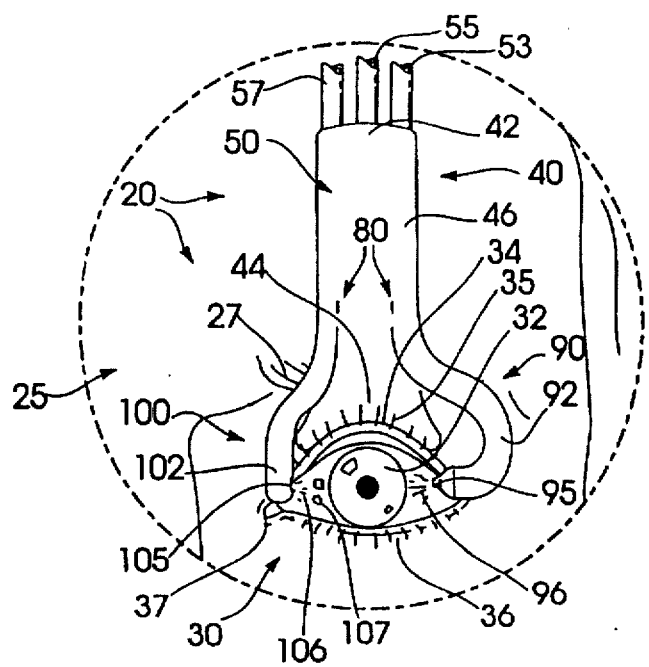
FIG. 2 is a greatly enlarged environmental view of the invention as shown in FIG. 1.
Figure 3:
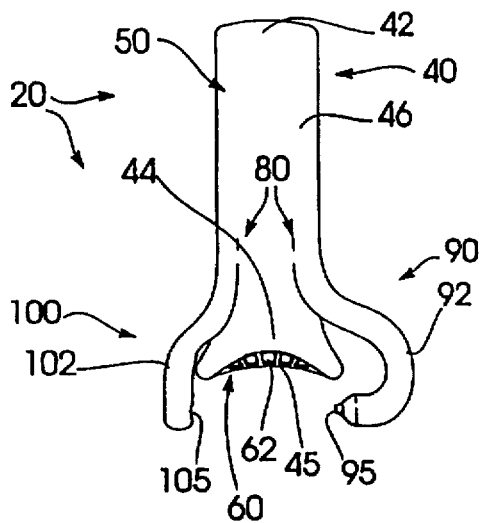
FIG. 3 is a front elevational view of the invention.
Figure 4:
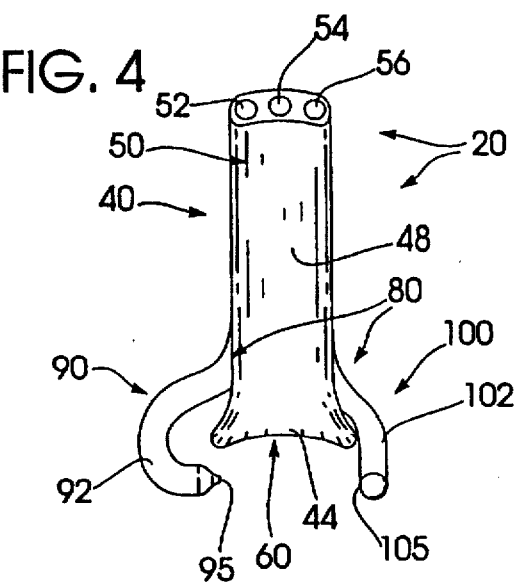
FIG. 4 is a rear elevational view of the invention.
Figure 9:
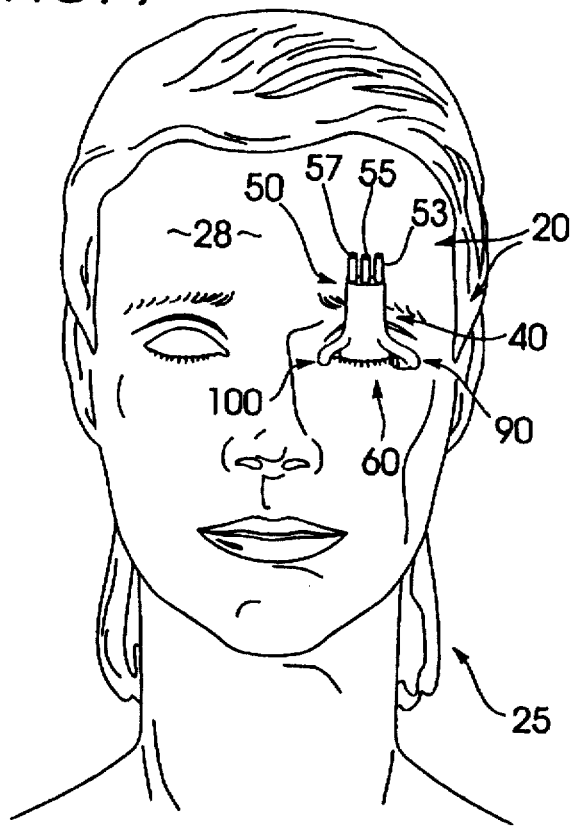
FIG. 9 is an environmental view taken generally from the front and showing the combined eyelid retractor and eye flushing device placed on a closed eyelid.
Figure 10:
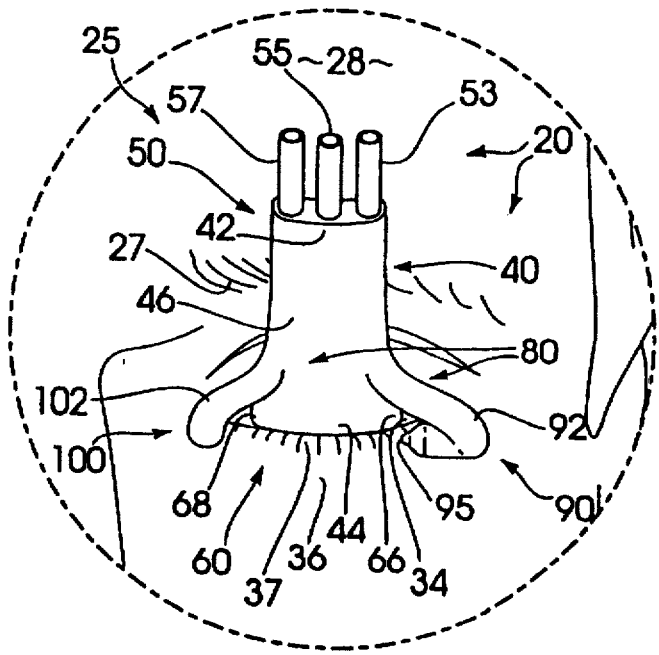
FIG. 10 is a greatly enlarged environmental view of the invention as shown in FIG. 9.
Figure 11:
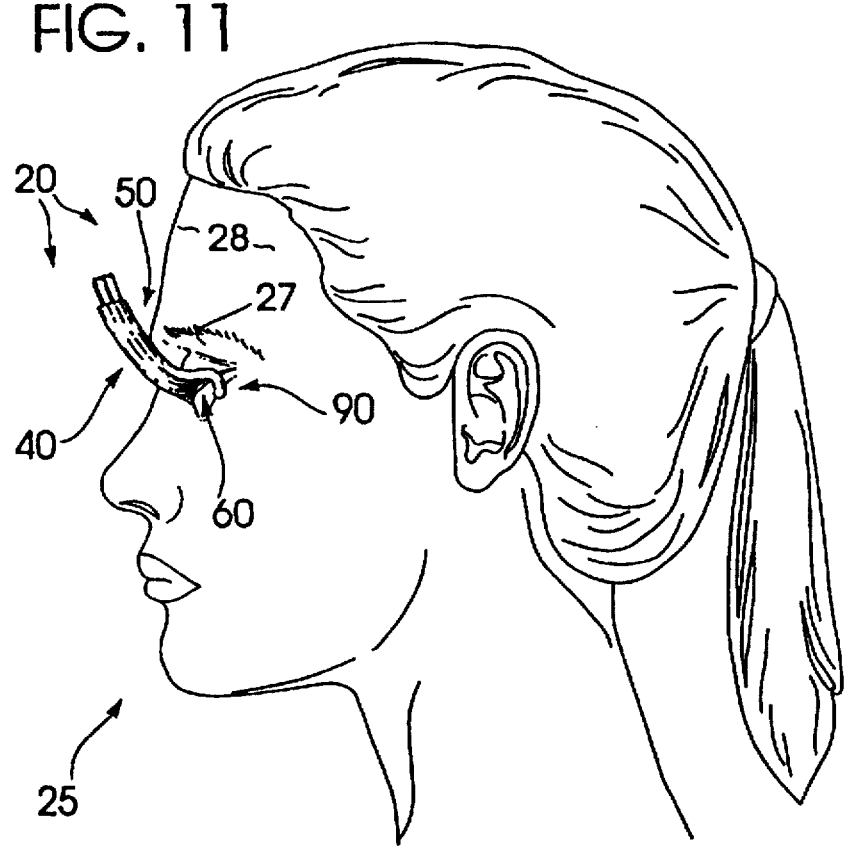
FIG. 11 is an environmental view taken generally from the side and showing the combined eyelid retractor and eye flushing device placed on a closed eyelid.

Referring more specifically to the drawings, my improved eyelid retracting and eye flushing device is generally designated by reference numeral 20 in FIGS. 1–14. My device 20 overcomes many of the problems perceived with known prior art devices. The device 20 permits an operator to retract the upper eyelid 34 of a patient 25 so that the eye 30 can be selectively flushed or otherwise treated (FIGS. 1–2). The device 20 comprises an elongated, resilient frame 40. The frame 40 forms an integral handle 50 adjacent one end 42. The other spaced apart frame end 44 forms an integral retractor lip 60. The frame 40 also supports an integral flushing system 80.

Figure 12:
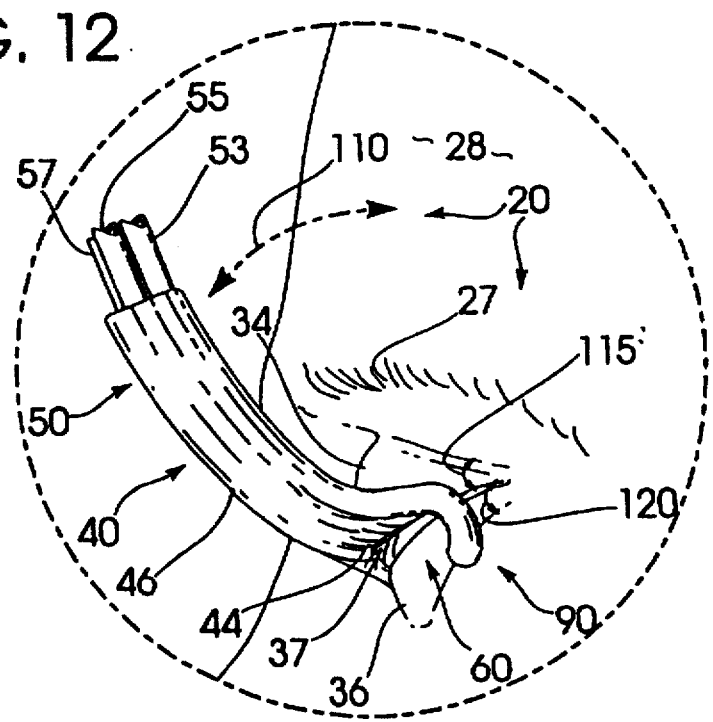
FIG. 12 is a greatly enlarged environmental view of the invention as shown in FIG. 11.
Figure 13:
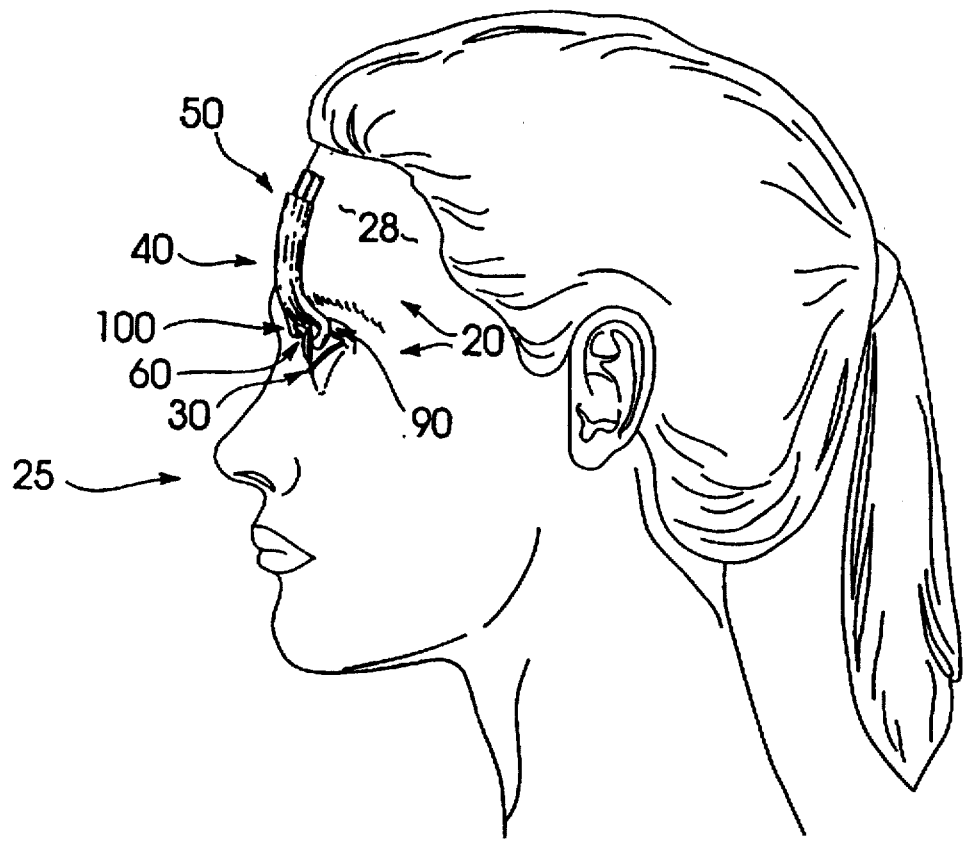
FIG. 13 is an environmental view taken generally from the side and showing the combined eyelid retractor and eye flushing device in a rotated position retracting the eyelid to open the eye to expose the eye; and, FIG. 14 is a greatly enlarged environmental view of the invention as shown in FIG. 13.
Figure 14:
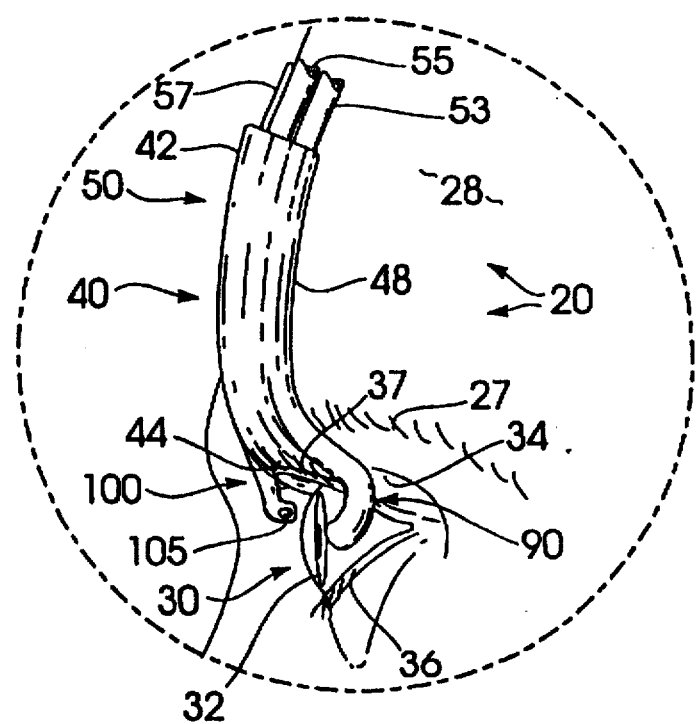

The handle 50 permits the operator to manipulate device 20 easily. The operator manipulates handle 50 to align and secure retractor 60 to the upper eyelid 34 of a patient 25 (FIG. 12). The eyelid 34 is preferably secured to the retractor 60 via vacuum suction from a conventional external source (represented by line 55 but not shown). Conventional vacuum sources typically provide suction between 10 and 20 pounds and the device preferably operates with around 15 pounds of suction.

The eyelid 34 may then be retracted to expose the interior of the eye 30, including the cornea 32, when the operator rotatably moves the device 20. Importantly, the placement and retraction of the eyelid 34 can be accomplished without exerting downward pressure upon the eye 30. During and after eyelid retraction, the eye 30 may be constantly flushed by an integral flushing system 80 to maintain corneal hydration. The flushing system 80 comprises an irrigator 90 that sprays liquids 96 from an external source (represented by line 53 but not shown) into the eye 30 and an aspirator 100 that captures the run-off liquids 106 and any entrained contaminants 107 and stores them externally (represented by line 57 but not shown).

The device 20 comprises an elongated, resilient frame 40 with spaced apart ends 42, 44 with a front 46 and a rear 48. The frame 40 forms an integral handle 50 abutting frame end 42.

Frame 50 permits convenient operator manipulation when device 20 is being deployed. A plurality of channels 52, 54 and 56 run through frame 40 inside handle 50. Each channel 52, 54 and 56 penetrates end 42 so that they may be conventionally coupled to external lines 53, 55 and 57 respectively.

The other frame end 44 has a peripheral edge 45 that forms an arcuate retractor lip 60 for securing the eyelid 34 to the frame 40. Preferably, a plurality of spaced apart orifices 62 penetrate the lip 60 so that the vacuum suction through the lip 60 is distributed along the entire surface of the edge 45. The flushing system 80 is also integrally attached to the frame 40 near the lip end 44.

In the preferred embodiment, the flushing system comprises an irrigator 90 and an aspirator 100. The irrigator 90 comprises a hollow stem 92 that protrudes outwardly from one side of the frame 40. The aspirator comprises another hollow stem 102 that protrudes outwardly from the other side of the frame 40. Thus, when the device is placed on a patient 25, the irrigation stem 92 protrudes from the outer side of the frame and the aspiration stem 102 protrudes from the inner side closest the patient's nose. The terminal end of the irrigation stem 92 forms a nozzle 95 adjacent the outer lip side 66. The terminal end of the aspiration stem 102 forms a terminal orifice 105 adjacent the inner lip side 68.

The lip 60, irrigator 90 and aspirator 100 all connect to the channels 54, 52 and 56 inside the frame 40 (connections not shown). The channels 54, 52 and 56 establish fluid flow communication through the frame 40 from the lip 60, irrigator 90 and aspirator 100 to external vacuum suction source line 55, liquid source line 53 and storage source line 57. As previously detailed, channels 52, 54 and 56 comprise conventional nipples adjacent end 42 to couple the channels to conventional medical tubing or the like.

Preferably, one channel 54 provides suction for the lip 60. Another channel 52 provides liquids for the irrigator 90 while yet another channel 56 provides communication to the external storage for the aspirator 100. The aspirator 100 may be powered by gravity, vacuum suction or the like. Of course, if vacuum suctioned, the aspirator 100 could use the same suction source as the lip 60 if desirable. On the other hand, the aspirator 100 could have a separate vacuum suction and storage source. In the preferred embodiment, the lip 60, irrigator 90 and aspirator 100 are all separately supplied and the aspirator 100 is vacuum suctioned.

Operation

When the device 20 is deployed on patient 25, the retractor lip 60 is placed along the lower edge of the upper eyelid 34 adjacent the eyelashes 35 by the operator. The operator simultaneously aligns the aspirator stem 102 over the inner terminus 37 of the palpebral fissure (the inner end of the upper-to-lower eyelid juncture). The upper eyelid is then seated against the frame edge 45 with vacuum suctioning through the lip 60. The operator may then retract the upper eyelid 34 by moving the frame handle 50 (as indicated by arrow 110 in FIG. 12) so that the frame rear 48 lies on the patient's forehead 28 and against the superciliary arch 27.

Thus, the operator can manipulate the eyelid using only one hand. Importantly, aseptic conditions are maintained because the operator does not need to actually touch the patient's eye during the placement or opening processes. As a result, the upper eyelid moves through the arc indicated by arrow 115 as it is retracted 34 and the lower eyelid 36 moves through the arc indicated by arrow 120 to open naturally.

After the eyelid 34 is seated against the lip 60, flushing may begin although most operators will prefer to wait until the eyelid 34 has been retracted before beginning eye flushing. Preferably, flushing is selectively controlled via conventional controls commonly used with liquid dispensing and vacuum suctioning. During flushing, the irrigator 90 sprays the liquid 96 across the eye 30 while the aspirator 100 drains run-off liquids 106 and entrained debris 107 from the eye 30.

When the operator finishes working upon the eye, the eyelid 34 may be released by simply turning off the vacuum suction. Of course, since the flushing is preferably selective, it is not difficult to cease flushing as well.

From the foregoing, it will be seen that this invention is one well adapted to obtain all the ends and objects herein set forth, together with other advantages which are inherent to the structure.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A device for non-invasively treating an eye, said device comprising:

means for initially opening an eyelid to expose a substantial portion of the eye in response to user manipulation of said device;

irrigation means for spraying liquids into said eye after said eye is opened; and, aspiration means for concurrently removing said sprayed liquids and any entrained debris leaving said eye.

2. The device as defined in claim 1 wherein said means for initially opening an eyelid comprises:

a frame an arcuate lip integrally defined upon said frame that contacts the exterior of the eyelid;

a plurality of spaced apart orifices penetrating said lip and said frame to establish a fluid flow pathway between said lip and said eyelid; and, vacuum means for suctioning said orifices, whereby said lip non-invasively retracts said eyelid without downward pressure being exerted on the surface of said eye.

3. The device as defined in claim 2 wherein said frame further comprises a plurality of internal channels, a first of said channels conducting said liquids to said irrigation means and a second of said channels conducting said suctioned liquids and entrained debris from said aspiration means and a third of said channels providing a fluid flow pathway between said vacuum means and said orifices.

4. The device as defined in claim 3 wherein said irrigation means comprises an irrigation stem in fluid communication with said first channel, said irrigation stem comprising a terminal nozzle for selectively spraying liquids into and across said eye after said eye is opened.

5. The device as defined in claim 3 wherein said aspirating means comprises an aspiration stem in fluid communication with said second channel, said aspiration stem protruding arcuately outwardly from said frame opposite said irrigation means and having a terminal orifice for suctioning liquids and any entrained debris leaving said eye.

6. The device as defined in claim 2 wherein said aspiration means further comprises means for aligning said lip when said lip is placed on said eyelid exterior.

7. The device as defined in claim 2 wherein said lip covers at least half of the lower edge of the upper eyelid when placed on said eyelid exterior.

8. A eye treatment device for non-invasively opening an eyelid without applying pressure while avoiding potential damage to the eye from trapped debris and the like, said device comprising:

an elongated resilient frame comprising spaced apart ends, one of said ends comprising a handle and the other of said ends comprising means for retracting said eyelid so that said eye can be opened to expose a substantial portion of the eye when said handle is moved by an operator, said means for retracting comprising:

an arcuate lip comprising a plurality of spaced apart orifices;

remote vacuum means for suctioning said orifices to retract said eyelid with said lip;

irrigation means for spraying liquids into said eye after said eye is opened; and, aspiration means for withdrawing sprayed liquids and said entrained debris leaving said eye.

9. The device as defined in claim 8 wherein said frame further comprises a plurality of internal channels, a first of said channels conducting said liquids to said irrigation means and a second of said channels suctioning said aspiration means and a third of said channels providing a pathway between said vacuum means and said orifices.

10. The device as defined in claim 9 wherein said irrigation means comprises an irrigation stem in fluid communication with said first channel, said irrigation stem protruding arcuately outwardly from said frame and having a terminal nozzle for selectively spraying liquids into said eye after said eye is opened to maintain corneal hydration.

11. The device as defined in claim 10 wherein said aspirating means comprises an aspiration stem in fluid communication with said second channel, said aspiration stem protruding arcuately outwardly from said frame opposite said irrigation stem and having a terminal orifice for receiving said sprayed liquids and any entrained debris leaving said eye.

12. The device as defined in claim 11 wherein said aspiration stem further comprises means for aligning said lip when said lip is placed on said eyelid exterior.

13. The device as defined in claim 8 wherein said lip covers at least half of the lower edge of the upper eyelid when placed on said eyelid exterior and said orifices spread said vacuum suctioning over at least a third of said lower edge.

14. A disposable device for aseptically retracting an eyelid so that a patient's eye may be selectively flushed to maintain corneal hydration, said device comprising:

an elongated resilient frame comprising spaced apart ends with a plurality of internal channels running between said ends;

means for non-invasively retracting said eyelid with said frame, said last mentioned means comprising an arcuate, peripheral edge that is suctioned by one of said channels;

an irrigation stem in fluid communication with another of said channels, said irrigation stem protruding arcuately outwardly from said frame and having a terminal nozzle for selectively spraying liquids into said eye; and, an aspiration stem in fluid communication with one of said channels, said aspiration stem protruding arcuately outwardly from said frame opposite said irrigation stem and having a terminal orifice for suctioning said sprayed liquids and any entrained debris leaving said eye.

15. The device as defined in claim 14 wherein said means for retracting further comprises:

remote vacuum means at one end of said suctioning channel for providing said suctioning; and, a plurality of spaced apart orifices penetrating said edge to establish a fluid flow pathway between said vacuum means and said eyelid so that said eyelid exterior is non-invasively secured to said edge to permit said eyelid to be retracted upwardly without downward pressure being exerted on the surface of said eye.

16. The device as defined in claim 15 wherein said aspiration stem further comprises means for aligning said edge when said edge is placed on said eyelid exterior.

17. The device as defined in claim 16 wherein said edge covers at least half of the lower edge of the upper eyelid when placed on said eyelid exterior and said orifices spread said vacuum suctioning over at least a third of said lower edge.

18. The device as defined in claim 17 wherein said device is adapted to be placed on said eyelid & to retract said eyelid by operator using only one hand.

* * * * *